US011299758B2

(12) United States Patent
Aymard et al.

(10) Patent No.: US 11,299,758 B2
(45) Date of Patent: Apr. 12, 2022

(54) METHOD FOR TREATING LIGNOCELLULOSIC BIOMASS BY IMPREGNATION

(71) Applicants: IFP Energies nouvelles, Rueil-Malmaison (FR); AGRO INDUSTRIES RECHERCHE ET DEVELOPPEMENT, Pomacle (FR); INSTITUT NATIONAL DE RECHERCHE POUR L'AGRICULTURE, L'ALIMENTATION ET L'ENVIRONNEMENT, Paris (FR)

(72) Inventors: Caroline Aymard, Lyons (FR); Pierre-Antoine Bouillon, Lyons (FR); Romain Rousset, Oullins (FR); Olivier Carnnot, Baconnes (FR)

(73) Assignees: IFP Energies nouvelles, Rueil-Malmaison (FR); AGRO INDUSTRIES RECHERCHE ET DEVELOPPEMENT, Pomacle (FR); INSTITUTE NATIONAL DE RECHERCHE POUR L'AGRICULTURE L'ALIMENTATION ET L'ENVIRONNEMENT, Paris (FR)

( * ) Notice: Subject to any disclaimer, the term of this patent is extended or adjusted under 35 U.S.C. 154(b) by 0 days.

(21) Appl. No.: 16/956,404

(22) PCT Filed: Dec. 4, 2018

(86) PCT No.: PCT/EP2018/083540
§ 371 (c)(1),
(2) Date: Jun. 19, 2020

(87) PCT Pub. No.: WO2019/120994
PCT Pub. Date: Jun. 27, 2019

(65) Prior Publication Data
US 2021/0087590 A1 Mar. 25, 2021

(30) Foreign Application Priority Data

Dec. 20, 2017 (FR) .................................. 17/62.611

(51) Int. Cl.
*C12P 7/10* (2006.01)
*C08H 8/00* (2010.01)
*C12P 19/00* (2006.01)
*C12P 19/02* (2006.01)

(52) U.S. Cl.
CPC .................. *C12P 7/10* (2013.01); *C08H 8/00* (2013.01); *C12P 19/00* (2013.01); *C12P 19/02* (2013.01); *C12P 2201/00* (2013.01)

(58) Field of Classification Search
CPC ........ C08H 8/00; C12P 19/02; C12P 2201/00; C12P 7/10; C12P 19/00
See application file for complete search history.

(56) References Cited

U.S. PATENT DOCUMENTS

| 8,057,639 | B2 | 11/2011 | Pschom et al. |
| 8,512,512 | B2 | 8/2013 | Pschom et al. |
| 8,597,431 | B2 * | 12/2013 | McDonald ............... C13K 1/02 127/1 |
| 8,609,379 | B2 | 12/2013 | Chheda et al. |
| 9,102,856 | B2 | 8/2015 | Cherchi et al. |
| 9,434,961 | B2 | 9/2016 | Dottori et al. |
| 10,307,932 | B2 | 6/2019 | Turnbull et al. |
| 2011/0318796 | A1 | 12/2011 | Walther |
| 2012/0104313 | A1 | 5/2012 | Garbero et al. |
| 2018/0258450 | A1 | 9/2018 | Dottori et al. |
| 2019/0241984 | A1 | 8/2019 | Hudebine et al. |

FOREIGN PATENT DOCUMENTS

| EP | 2610346 | B1 | 7/2014 | |
| WO | 10121367 | A1 | 10/2010 | |
| WO | 12061939 | A1 | 5/2012 | |
| WO | 12088108 | A1 | 6/2012 | |
| WO | 15173226 | A1 | 11/2015 | |
| WO | 18015227 | A1 | 1/2018 | |
| WO | WO2018015227 | A1 * | 1/2018 | ............... C08H 8/00 |

OTHER PUBLICATIONS

Gillet et al., Lignin transformations for high value applications: towards targeted modifications using green chemistry. Green Chem., 2017, vol. 19: 4200-4233. (Year: 2017).*
Long et al., Catalytic delignification of sugarcane bagasse in the presence of acidic ionic liquids. Catalysis Today, 2013, vol. 200: 99-105 (Year: 2013).*
International Search Report wo2018ep083540 dated Jan. 24, 2019 (pp. 1-3).

* cited by examiner

*Primary Examiner* — Ganapathirama Raghu
(74) *Attorney, Agent, or Firm* — Millen White Zelano & Branigan, PC

(57) ABSTRACT

The invention relates to a process for treating lignocellulosic biomass by means of an acidic liquor in order to produce "second-generation" (2G) sugary liquors. These sugary liquors may be used to produce other products via a biochemical pathway (e.g. alcohols such as ethanol, butanol or other molecules, for example solvents such as acetone, etc.). This process comprises analysis of the liquid streams withdrawn during the process and adjustment of the composition of the impregnation liquor so as to keep the acidic power of said streams constant.

19 Claims, 2 Drawing Sheets

METHOD FOR TREATING LIGNOCELLULOSIC BIOMASS BY IMPREGNATION

FIELD OF THE INVENTION

The invention relates to a process for treating lignocellulosic biomass by means of an acidic liquor in order to produce "second-generation" (2G) sugary liquors. These sugary liquors may be used to produce other products via a biochemical pathway (e.g. alcohols such as ethanol, butanol or other molecules, for example solvents such as acetone, etc.). This process comprises analysis of the liquid streams withdrawn during the process and adjustment of the composition of the impregnation liquor so as to keep the acidic power of said streams constant.

PRIOR ART

Lignocellulosic biomass represents one of the most abundant renewable resources on Earth. The substrates considered are very varied, they relate both to ligneous substrates such as various woods (hardwoods and softwoods), coproducts derived from agriculture (wheat straw, corn cobs, etc.) or from other agrifood, paper, etc. industries.

The process for the biochemical conversion of the lignocellulosic material into 2G sugary liquors notably comprises a pretreatment step and a step of hydrolysis with an enzymatic cocktail. These processes also usually include an impregnation step before the pretreatment. The sugary liquors resulting from the enzymatic hydrolysis are then treated, for example by fermentation, and the process also comprises separation steps and/or a step of purification of the final product.

Lignocellulosic biomass is composed of three main polymers: cellulose (35% to 50%), which is a polysaccharide essentially constituted of hexoses; hemicellulose (20% to 30%), which is a polysaccharide essentially constituted of pentoses and hexoses; and lignin (15% to 25%), which is a polymer of complex structure and of high molecular weight, composed of aromatic alcohols connected via ether bonds. These various molecules are responsible for the intrinsic properties of the plant wall and organize themselves into a complex entanglement. Besides these three major compounds, lignocellulosic biomass also notably contains acetyl groups and ash. This "ash" is composed of minerals: silica, compounds containing calcium, magnesium, sodium, potassium, phosphorus and/or aluminum.

Their content and their composition vary enormously from one type of biomass to another (straw versus wood, etc.), but also as a function of the pedoclimatic culture conditions and the harvesting conditions. Different batches of straw will have variable natures of ash in different contents. One method for quantifying the ash of lignocellulosic products is described, for example, in the standard ASTM E1755 "Standard Test Method for Ash in Biomass".

Among the three base polymers that make up the lignocellulosic biomass, cellulose and hemicellulose are the ones that enable the production of 2G sugary liquors.

Usually, hemicellulose is predominantly broken down into sugar during the pretreatment and cellulose is converted into glucose by enzymatic hydrolysis. However, access to crude cellulose remains difficult for enzymes to access, hence the need for a pretreatment. This pretreatment makes it possible to modify the physicochemical properties of the lignocellulosic material in order to improve the accessibility of the cellulose to enzymes and its reactivity to enzymatic hydrolysis.

One of the most effective pretreatments is acidic steam explosion which enables almost complete hydrolysis of hemicellulose and a significant improvement in the accessibility and reactivity of cellulose with respect to enzymes. This pretreatment may be preceded by other treatment(s).

U.S. Pat. Nos. 8,057,639 and 8,512,512 propose a process comprising a first step of hydrolysis of hemicellulose to C5 sugars under mild conditions which thus protect them from degradation. This step is performed in a first reactor at a pressure of 1.5 bar or more by injection of steam, at a temperature of 110° C. or more, and optionally in the presence of a weak acid. After this step, washing is performed in order to extract and recover the C5 sugar juices before sending the remaining biomass, enriched in cellulose and lignin, to a second step (second reactor) where the steam explosion takes place. This second reactor operates at a higher pressure than the first reactor with an injection of high-pressure steam which causes a sudden expansion of the biomass (steam explosion).

Patent application US-2012/0104313 also proposes a treatment step prior to steam explosion by contacting the biomass with water or steam at 100-210° C. for 1 min-24 h. After separation of the hemicellulose-enriched liquid phase, the solid is then transferred to the steam explosion step.

Patent EP 2610346 describes a process for treating lignocellulosic biomass in four steps: a treatment in a liquid at a temperature of 100-150° C., followed by a separation of the liquid/solid, followed by a pretreatment of the solid part obtained at 100-210° C. in the presence of water or steam for 1 min-24 h and finally a liquid/solid separation.

In the context of its research, the Applicant has demonstrated that it is possible to more significantly improve the performance of the known biomass pretreatment processes. Specifically, the presence of ash and of acetyl groups in variable amounts in the biomass is liable to modify the properties thereof. However, measuring the ash content and assaying the acetyl groups is expensive in terms of time and difficult to implement to enable continuous monitoring of a process.

The Applicant has thus found that by adjusting the composition of the impregnation liquor as a function of the acidic power of the liquid streams obtained from the biomass pretreatment process (liquor separated out after impregnation and/or any one of the liquid streams withdrawn during the biomass pretreatment), it is possible to significantly improve the performance and stability of the biomass treatment process. It is in fact thus possible, by real-time adjustment of the composition of the impregnation liquor used, to counteract the intrinsic variability of the biomass and to ensure the stability of the downstream performance, in particular in terms of reactivity of the treated biomass with cellulases.

SUMMARY OF THE INVENTION

Thus, the present invention proposes a process for the continuous treatment of a lignocellulosic biomass for the production of sugary liquors, comprising the following steps:

a) impregnating the biomass using an impregnation liquor with a pH of between 0.1 and 7, by placing said biomass in contact with said impregnation liquor, b) separating the impregnated biomass obtained in step a) so as to produce a wet biomass with a solids content of at least 15% by weight, and a separated liquor, c) pretreating the wet biomass obtained in step b) to produce a pretreated biomass, in the course of which one or more liquid streams are withdrawn, characterized in that it comprises d) analysis of the composition of the liquor separated out obtained from step b) and/or of one or more of the liquid streams withdrawn during the biomass pretreatment, and e) adjustment of the composition of the impregnation liquor used in step a) so as to keep constant the acidic power of said liquor separated out obtained from step b) and/or of said liquid streams withdrawn during the biomass pretreatment, throughout the process.

For the purposes of the present patent application, the term "sugary liquors" means any aqueous mixture of sugars obtained from lignocellulose, for example glucose, xylose, mannose, galactose and arabinose.

It is, in point of fact, to the Applicant's credit to have demonstrated that it is possible to compensate for the intrinsic variation in biomass composition to ensure that the treated biomass always has substantially the same level of reactivity toward cellulases. The Applicant has in fact discovered that by controlling the acidic power of certain liquid streams generated in the process, and by adjusting the composition of the acidic impregnation liquor so as to keep this acidic power constant, it is possible to regulate the biomass treatment processes, despite the intrinsic composition variations thereof.

In the context of the present invention, the abbreviation "SC" denotes the solids content of the biomass, which may in particular be measured according to the standard ASTM E1756-08(2015) "Standard Test Method for Determination of Total Solids in Biomass".

DETAILED DESCRIPTION

The process according to the invention is a continuous process for treating a lignocellulosic biomass before enzymatic hydrolysis.

It is integrated into processes directed toward producing second-generation sugars from which many biochemical pathways make it possible to obtain oxygenated molecules (for example alcohols such as ethanol, butanol, etc.).

This process is compatible with the processes for producing 2G sugars (i.e. those obtained from lignocellulosic biomass) or more broadly biobased molecules (i.e. molecules from natural substrates or derived from natural substrates).

Biomass

The process according to the invention proposes to continuously treat a lignocellulosic biomass.

This biomass may originate from varied sources, such as ligneous substrates such as various woods (hardwoods and softwoods), coproducts derived from agriculture (wheat straw, corn cobs, etc.) or from other agrifood, paper, etc. industries.

Depending on the biomass used (straw, wood, etc.), a milling step, prior to its use in the process of the invention, may be envisaged to obtain a particle size that is compatible with the technological means and the operating conditions of the steps of the process. For this, simple chipping may be sufficient but milling, with or without refining, may be required.

In general, the biomass used in step a) of the process of the invention has a particle size (the largest size) of not more than 300 mm. Usually, the milling of straw is performed with screens of from 5 to 100 mm and wood is chipped into parallelepipedal chips with a length of between 20 and 160 mm, a width of between 10 and 100 mm and a thickness of between 2 and 20 mm.

The biomass is preferably conveyed to the impregnation step via a first transfer zone. According to a particular embodiment, the transfer zone and the impregnation zone may be separated by a biomass plug which prevents liquid backflow from said first zone to the transfer zone or even further upstream.

Impregnation Liquor Preparation Step

The impregnation liquor used in the process according to the invention is preferably an acidic liquor, comprising at least one acid, and optionally water.

Specifically, certain biomasses have a very low solids content (for example less than 50% SC) and thus a water content that is high enough for it not to be necessary to add more water in order to perform the impregnation. In this case, the impregnation liquor is prepared by introducing only acid, which will be mixed, during the impregnation step, with the water already present in the biomass.

In particular, the acidic liquor has a pH of between 0.1 and 7.0, preferably between 0.1 and 6 and preferentially between 0.1 and 2.

According to a preferred embodiment, the liquor comprises at least one acid and water.

Preferably, the acidic liquor is an aqueous solution of a strong acid, chosen, for example, from sulfuric acid, hydrochloric acid and nitric acid at an acid content of between 0.5% and 8% by weight of acid relative to the total weight of the liquor. According to a preferred embodiment, the impregnation liquor is a sulfuric acid solution.

This type of liquor is well known to those skilled in the art and any acid customarily used for impregnation is suitable for use. The amount of acid and the temperature of the liquor are generally fixed. The means for obtaining and maintaining the temperature are known to those skilled in the art.

The process according to the invention may involve a step of preparing the impregnation liquor prior to the impregnation step a).

In this step, the impregnation liquor is preferably heated to a temperature ranging from 10 to 95° C. This step may be performed in a liquor preparation zone located upstream of the impregnation zone.

Various devices may be used, for instance a mixing tank equipped with a stirring system or a mixer (preferably a static mixer). Preferably, the device is equipped with sensors for measuring the pH and the flow rate for the water, acid and the recycled liquor. All of these sensors makes it possible to put in place a control that balances the flow rates and the acidities so as to have a continuous operation that is stable under the desired conditions.

The liquor preparation device may be equipped to allow the heating of its contents by means, for example, of a jacket, coils and/or exchangers positioned on the recirculation loop (described below) next to or directly on said devices (tank, mixer, etc.). The device used for the preparation of the liquor may notably be connected to the impregnator via one or more pipes that transport the liquor.

The liquor may thus be prepared with a suitable concentration and suitable flow rate which make it possible to obtain the desired acidic power for the liquid streams withdrawn downstream of the impregnation.

The liquor preparation is also a step that makes it possible to regulate its operating parameters, for instance the temperature, the pH or any other feature. The appropriate acid concentration is regulated by means of inputs of acid and/or water.

Impregnation Step

The process according to the invention involves a step a) of impregnating the biomass using an impregnation liquor with a pH of between 0.1 and 7, by placing said biomass in contact with said impregnation liquor.

Preferably, in the process according to the invention, the impregnation step is performed at a temperature ranging from 10 to 95° C., and the residence time of the biomass in said impregnation step is between 20 seconds and 12 hours. Preferably, the residence time of the biomass is between 30 seconds and 60 minutes. The impregnation step is preferably performed at atmospheric pressure.

The impregnation step is performed by placing the biomass in contact with the impregnation liquor. This placing in contact may be performed, for example, by dipping or by spraying. During the impregnation, it is generally preferable to keep the level of liquor virtually constant by supplying impregnation liquor.

The impregnation step may be performed in batch or continuous mode. Preferably, this step is performed in continuous mode. The impregnation may be performed in one or more impregnation reactors, preferably in a single impregnation reactor.

The impregnation step is performed in equipment known to those skilled in the art, for example in a stirred reactor, by horizontal or vertical throughput of the biomass in a bed of liquor, by spraying on a belt transporting the biomass or in a transportation screw.

The impregnation reactor (or impregnator) is generally equipped with one or more tools which transfer the lignocellulosic biomass from its entry to the outlet aperture. These tools may be, for example, screws or belts. The impregnator is moreover equipped with one or more pipes for conveying the acid, the water or the acidic liquor and also, optionally, one or more pipes for withdrawing acidic liquor.

According to a preferred embodiment, the biomass impregnated with liquor may be drained during the impregnation in order to extract at least some of the acidic liquor, before being sent to the separation step b). In this embodiment, the solids content of the drained biomass is between 10% and 40% by weight and preferably between 15% and 30% by weight.

The impregnation reactor (impregnator) may be equipped with one or more pipes for conveying the impregnation liquor when it is prepared in a prior step, and also one or more pipes for introducing water and/or acid, and for removing liquor.

According to a very particular embodiment, the impregnation step may be performed in an impregnation reactor (or impregnator) of tubular shape which is vertical or inclined with an angle of less than 60° with respect to the vertical. This reactor notably includes two superposed impregnation zones that are preferably located on the same axis. The bottom zone is referred to as the first impregnation zone and receives, through an aperture, the pressed biomass obtained from the first transfer zone. The zone located above (top zone) is referred to as the second impregnation zone, and it receives the wet drained biomass originating from the first impregnation zone. In this embodiment, the impregnation reactor (impregnator) may be equipped with one or more transportation screws which transfer the biomass via the bottom of the first impregnation zone to the outlet aperture via the top of the second impregnation zone. The first impregnation zone (therefore the zone where the impregnation of the biomass with the impregnation liquor takes place) corresponds to the space filled with the impregnation liquor. The second impregnation zone does not in particular contain any continuous liquid phase. It is particularly advantageous to maintain a constant distribution between the first impregnation zone and the second impregnation zone. To do this, the reactor is equipped with a detection system (level sensor), preferably with a system for regulating the level of liquor, which makes it possible to ensure filling to the desired level. The effect of compressing the biomass during the formation of the plug (at the transfer screw conveying the biomass to the impregnation step) and of decompression at the inlet of the first impregnation zone filled with liquor makes it possible to better saturate the biomass (sponge effect). The biomass is transferred across the first zone where it is impregnated toward the second impregnation zone located above the level of the liquor. In the second impregnation zone, a portion of the impregnated liquor is separated from the impregnated biomass by draining during the rise into the second impregnation zone, the drained liquor being extracted from the second impregnation zone to be recycled. Preferably, the second impregnation zone is equipped with screen(s) retaining the wet biomass in the second impregnation zone, which screen therefore allows the drained liquor to flow from the second impregnation zone into the first impregnation zone.

Impregnated Biomass Separation Step

On conclusion of the impregnation step a), the process according to the invention involves a step b) of separating the impregnated biomass obtained in step a) so as to produce a wet biomass with a solids content of at least 15% by weight, and a separated liquor.

The separation step may be performed via any technique known to those skilled in the art, for example by draining, decantation, centrifugation or pressing of the impregnated biomass, or a combination of these techniques. According to a preferred embodiment, the separation is performed by pressing.

In particular, the separation step b) may comprise draining the wet biomass to reach a solids content of between 10% and 40% by weight, followed by a second separation, for example by pressing, to reach a higher solids content of between 40% and 70%. This embodiment is particularly preferred when no draining has been performed during the impregnation step a).

Preferably, on conclusion of the separation step b), the wet biomass has a solids content of between 25% and 70% by weight and preferably between 40% and 65% by weight.

In one particular embodiment of the invention, pressing of the wet biomass may be performed concomitantly with its transfer into the pretreatment step c), notably when said step involves the cooking process that is described below. This implementation of the separation step b) is performed, for example, by means of a screw known as a plug screw feeder, which is known to those skilled in the art. This screw has a conical-shaped part, said conical part being connected to the inlet of the pretreatment reactor. A biomass plug becomes created at the end of this conical part just before the inlet into the pretreatment reactor. The formation of a pressed lignocellulosic biomass plug ensures the pressure-tightness of the cooking reactor which may be used in the pretreatment step c). The transfer screw may also be equipped with one or more pipes for withdrawal of the spent liquor (known as the press liquor) separated out during the pressing.

Substantial extraction of the spent impregnation liquor during the present process makes it possible to substantially increase the solids content of the biomass for its subsequent treatment and its transformation into sugars. The production of a biomass with a high solids content may allow energy savings for heating the medium to the desired pretreatment temperature, and may make it possible to obtain a pretreated biomass which also has a high solids content SC. The conveying of the pretreated biomass into the following enzymatic hydrolysis step is thus facilitated, and the enzymatic hydrolysis of a biomass with a high SC makes it possible to obtain a concentrated (hydrolyzed) sugar solution, making it possible to target high fermentation titers (alcohol content), and thus to reduce the costs associated with the separation steps, notably by distillation, for the profitable exploitation of these alcohols. Moreover, performing the process while maintaining a high biomass solids content makes it possible to reduce the volume of the fermentation (and hydrolysis) tanks and to reduce the amount of spent waters generated by the process.

The separation zone used in step b) may notably be equipped with a pipe for withdrawing the resulting spent liquor (known as the press liquor) separated from the wet biomass.

Pretreatment Step

The process according to the invention also involves a step c) of pretreating the wet biomass obtained in step b) to produce a pretreated biomass, in the course of which one or more liquid streams are withdrawn.

The pretreatment is notably directed toward modifying the physical and physicochemical properties of the cellulosic fraction, such as its degree of polymerization and its state of crystallinity. In particular, the pretreatment comprises hydrolysis of the hemicellulose present in the biomass and allows better accessibility of the cellulose to the enzymes.

According to a preferred embodiment, step c) of pretreating the wet biomass is performed by cooking, preferably by steam explosion.

This cooking is performed, for example, in a cooking zone operating at a temperature of between 100° C. and 250° C. and more preferentially between 130° C. and 230° C., at a pressure of between 0.1 and 4 MPa. The residence time of the biomass in the cooking zone is between 10 seconds and 4 hours and more preferentially between 3 minutes and 1 hour.

The cooking may take place in batch or continuous mode. It may be performed in any equipment known to those skilled in the art, for example a stirred reactor, a horizontal tubular reactor equipped with a transportation screw, a non-stirred batch reactor, etc. The thermal energy required for the cooking may be supplied via a heat exchange with a heat-transfer fluid (indirect), by electrical heating, or by direct injection of a hot fluid, for example pressurized water or steam.

The exit of the pretreated biomass at the end of cooking may take place by rapid decompression, by slow decompression, after a temperature reduction induced by direct or indirect heat exchange, etc.

In a preferred embodiment, the cooking zone is heated with steam by direct injection and is followed by abrupt decompression of the medium, this process being known as steam explosion (or "steamex"). This is a process in which the lignocellulosic biomass is rapidly brought to a high temperature by injecting pressurized steam. Stoppage of the treatment takes place by abrupt decompression.

The operating conditions of the steam explosion process may notably be as follows:

steam is injected directly into the reactor;
the temperature of the reactor is generally between 150 and 250° C. and preferably between 160° C. and 220° C.,
the pressure is between 0.5 and 2.5 MPa, more preferentially between 0.8 and 2.0 MPa,
the residence time before the expansion phase ranges from 10 seconds to 25 minutes and preferably between 3 minutes and 15 minutes.

The steam explosion may be performed in batch or continuous mode and the depressurization step which permits destructuring of the biomass may proceed in one or more steps.

During the pretreatment step, various liquid streams may be withdrawn. These are notably hot fluids (liquid or vapor) injected to perform the pretreatment, such as pressurized water or steam.

The steam recovered is advantageously recycled after compression into the steam explosion step, or optionally is recycled into the utilities of the site.

According to a particular embodiment, the pretreatment step may be performed in a horizontal tubular reactor (i.e. a reactor which may be very slightly inclined for the flow of the liquid), for example equipped with a screw for transferring the biomass through the successive zones. The screw ensures the transportation of the biomass continuously, the speed of the screw being regulated in order to fulfil the residence time conditions. At the end of the screw (at the end of the reactor), the biomass is entrained very rapidly by the steam to an expansion zone in a line referred to as a blowline which has a reduced diameter relative to the cooking zone. The expansion zone comprises a line in which the biomass circulates and passes through a cross section restriction member then, after having cleared the restriction, undergoes an abrupt expansion. The blowline has a cross section restriction member which may be an orifice or a valve with an adjustable aperture (diaphragm valve, for example) that allows a small flow area. At this restriction, the biomass arrives with a very high transportation speed, and undergoes a rapid and large pressure variation, then an abrupt expansion after having cleared the restriction, which destructures the cooked biomass. This is why it is referred to as steam explosion. Once the expansion zone is passed, the biomass is entrained by the steam through the remainder of the blowline which has a larger diameter than the restriction (or which returns to its diameter upstream of the restriction) and which conveys the biomass to a zone for separating out the steam, for example by means of a cyclone.

The pretreated biomass obtained from step c) now has a sufficient accessibility of the cellulose to enzymes in order to be treated by enzymatic hydrolysis for the production of 2G sugars.

Analysis of the Fluidity of the Streams and Adjustment of the Composition of the Impregnation Liquor The process according to the invention is characterized in that it involves a step d) of analysis of the composition of the liquor separated out obtained from step b) and/or of one or more of the liquid streams withdrawn during the biomass pretreatment.

In particular, the liquid streams withdrawn during the biomass pretreatment are liquid streams withdrawn downstream of the impregnation step a) and upstream of the subsequent biomass treatment steps, in particular upstream of the cooking step.

According to a preferred embodiment, step d) involves analysis of the composition of the liquor separated out obtained from step b) (known as the press liquor).

Specifically, it is to the Applicant's credit to have demonstrated that controlling the composition, and in particular the acidic power, of the liquid separated out obtained from step b) and/or of one or more of the liquid streams withdrawn during the biomass pretreatment could make it possible to counterbalance the intrinsic variability of the biomass and to ensure the stability of the downstream performance, in particular in terms of reactivity of the treated biomass with cellulases.

In particular, the analysis of the composition of the liquor separated out obtained from step b) and/or of one or more of the liquid streams withdrawn during the pretreatment involves measuring the acidic power of said liquor separated out obtained from step b) and/or of said liquid streams withdrawn during the biomass pretreatment, throughout the process, preferably by measuring the pH of said liquor and/or of said liquid streams, the measurements notably being taken continuously or at a given frequency.

The acidic power is defined as the amount of $H^-$ ions present in the liquid under consideration. It may be measured by various parameters, by methods that are well known to those skilled in the art. The acidic power may be measured, for example, by assaying the acids contained in the solution by titrimetry (monitoring of the change in pH during a phased addition of a base solution), by measuring the pH of the solution and/or by measuring the conductivity of said solution. Ideally, when the equipment for measuring the pH is sufficiently accurate, measurement of the pH of the liquids is preferred for characterizing the acidic power.

When the pH levels are very low and there is a risk of the pH measurement not giving sufficiently accurate results, this measurement may preferably be accompanied by a conductivity measurement.

The pH of the liquor separated out obtained from step b) and/or of one or more of the liquid streams withdrawn during the pretreatment is preferably between 0.1 and 7, preferably between 0.5 and 4, and more preferably between 0.7 and 2.5.

The conductivity of the liquor separated out obtained from step b) and/or of one or more of the liquid streams withdrawn during the pretreatment may, itself, be between 5 and 250 mS/cm and more preferentially between 15 and 150 mS/cm, when it is measured at 70° C.

The process according to the invention involves controlling the composition of the impregnation liquor used in step a) so as to keep constant the acidic power of at least one of the liquid streams withdrawn during the process of the invention.

In particular, the process according to the invention involves a step e) of adjusting the composition of the impregnation liquor used in step a) so as to keep constant the acidic power of said liquor separated out obtained from step b) and/or of said liquid streams withdrawn during the biomass pretreatment, throughout the process.

For the purposes of the present patent application, it is understood that the acidic power is "kept constant" when the magnitude which characterizes it (pH, conductivity, assay of the acids, etc.) generally does not vary by plus or minus 10% to 20% throughout the functioning of the process. Thus, in particular, the composition of the impregnation liquor should be adjusted so as to ensure that the pH of the liquor separated out obtained from step b) and/or of said liquid streams withdrawn during the biomass pretreatment does not vary by more than 20% about its initial value, preferably by plus or minus 10% about its initial value (thus, notably, to within ±20%, preferably to within ±10% of the target acidic power value). For very low pH values, typically below 1.5, stability of the pH is considered as a variation of plus or minus 0.1 pH unit about the nominal value. According to a particular embodiment, when the acidic power is characterized by the conductivity, the composition of the impregnation liquor should be adjusted so as to ensure that the conductivity of the liquor separated out obtained from step b) and/or of the liquid streams withdrawn during the biomass pretreatment does not vary by more than 20% about its initial value, and preferably not more than 10% about its initial value.

Thus, when the acidic power of the stream under consideration decreases during the functioning of the process according to the invention, the acidity of the impregnation liquor introduced into step a) is increased (by lowering the pH), and, conversely, when the acidic power of the stream under consideration increases during the functioning of the process according to the invention, the acidity of the impregnation liquor introduced into step a) is reduced (by dilution).

In particular, the adjustment is performed by adding (or supplying) water and/or acid to said impregnation liquor used in step a).

The additions of water or of acid may be made either directly into the biomass impregnation step a), or during the preparation of the impregnation liquor. It may be performed directly on the line or in equipment (mixer, tank or the like).

Recycling Step

According to a particular embodiment, the process according to the invention involves a step of recycling of the liquor separated out obtained from step b), of the liquid streams withdrawn during the biomass pretreatment and/or of the liquid streams withdrawn during the subsequent biomass treatment steps, for example by enzymatic hydrolysis and/or alcoholic fermentation, into the impregnation step a).

In the case where recycling is performed, the adjustment of the composition of the impregnation liquor is proportionately larger the more variable the acidic power of the recycled streams.

Specifically, the Applicant has demonstrated that the impregnation gave rise to spent liquors (press liquor and drained liquor) depleted in acid and liquid streams withdrawn during the biomass pretreatment which have a residual acidity. Without wishing to be bound by a theory, it is possible that these acidity variations may be due to a basicity of the biomass which neutralizes part of the acid of the impregnation liquor introduced into the process of the invention. Surprisingly, these streams, notably the spent liquor, also have a buffer effect which may be due to the extractable matter of the biomass. Thus, recycling them significantly modifies the properties of the impregnation liquor. By making the additions of water and of acid described in the present patent application, the Applicant has thus observed that it is possible to compensate for the variations in the quality of the impregnation liquor associated with the recycling so as to keep constant the satisfactory properties in terms of cellulase reactivity of the treated biomass.

Thus, when recycling of one or more liquid streams of the process is performed, their composition is analyzed in the same way as that of the liquor separated out obtained from step b) or of the liquid streams withdrawn during the biomass pretreatment, and the composition of the impregnation liquor used in step a) is adjusted so as to keep constant the acidic power of said recycled liquid streams, throughout the process.

In the context of the present process, a liquor having the desired pH is thus prepared to maintain good impregnation throughout the process. One portion of the added acid makes it possible to counter the basicity of the biomass which can be measured beforehand. A second portion of this addition makes it possible to counter the buffer nature of the spent liquors. The water additions make it possible to adjust the flow rate of impregnation liquor introduced into step a).

In certain cases, one or two purges may also be installed just after the separation of the liquor performed in step b) (pressing or draining) to prevent excessive concentration of molecules obtained from the biomass.

It is also possible to envisage a step of treating the liquor to be recycled in order to purify it and to reduce the use of purging.

Similarly, in certain cases, it is possible to use, for the additions, various water sources originating from the process in which the impregnation/pretreatment line is incorporated. For example, the water addition may come from the treatment of the waters, of the vinasses obtained from the first distillation column or from the phlegms originating from certain cuts of the main distillation, or a combination of streams of this type. These vinasses and these phlegms may optionally undergo a treatment to be purified.

Treatment of the Pretreated Biomass by Enzymatic Hydrolysis and Alcoholic Fermentation The process according to the invention may in particular comprise, after the pretreatment step c), a step of treating at least a part of the pretreated biomass, by enzymatic hydrolysis, to produce said sugary liquors. According to a preferred embodiment, at least one portion of the sugary liquors is subjected to an alcoholic fermentation.

The conditions of the enzymatic hydrolysis and of the consecutive or simultaneous fermentation are suitable for the desired products and are known to those skilled in the art.

The process according to the invention finds a particularly advantageous application in a process for preparing sugars from lignocellulosic biomass and in the process for producing ethanol from said sugary liquors. Such processes are known. A process for preparing sugars from lignocellulosic biomass includes a pretreatment, which is advantageously steam explosion, followed by enzymatic hydrolysis. The process for producing ethanol from sugars also comprises alcoholic fermentation of said sugars.

In the context of the present process, the flow rates of the impregnation liquor, of the water and of the liquors separated out (press liquor or drained liquor) are measured with any equipment known to those skilled in the art (for example a flowmeter, level in a volume, or the like).

DETAILED DESCRIPTION OF THE DRAWINGS

Figure 1:
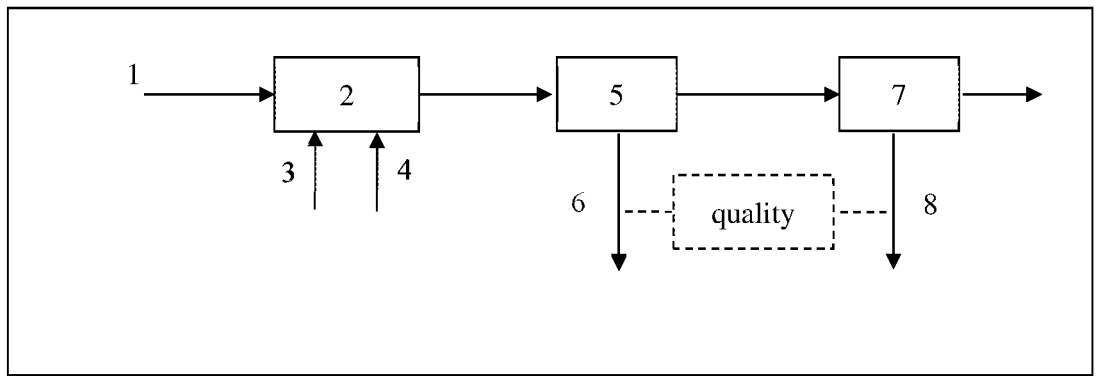
FIGS. 1 to 4 of the present patent application illustrate, in a nonlimiting manner, the implementation of the process according to the invention.

As shown in FIG. 1, the milled biomass is introduced via pipe 1 into the impregnation zone 2. This zone contains the impregnation liquor, composed of acid introduced via pipe 3, and optionally water introduced via pipe 4.

The milled biomass is introduced via pipe 1 into the impregnation zone 2. This zone contains the impregnation liquor, composed of acid introduced via pipe 3, and optionally water introduced via pipe 4.

Figure 2:
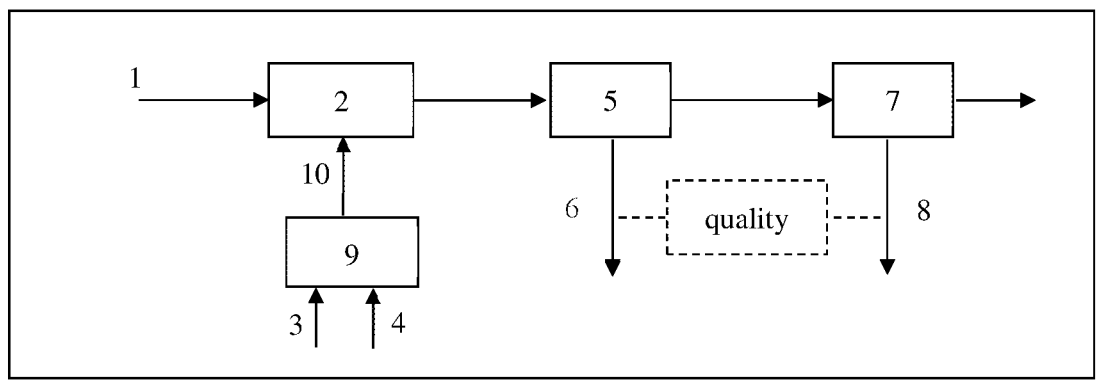

In the embodiment illustrated in FIG. 2, the impregnation liquor is prepared in a step prior to the impregnation, in a liquor preparation zone 9, by introducing acid (3) and optionally water (4). The liquor thus prepared is introduced into the impregnation zone 2 via pipe 10.

The impregnated biomass obtained is then transferred to a separation zone 5 so as to produce a wet biomass and a separated liquor 6.

According to one embodiment, the features of the separated liquor 6 are measured by means of sensors (pH, conductivity, flow rate, etc.) and the amounts of acid and/or of water introduced via pipes 3 and 4 are adjusted so as to keep constant the acidic power of said separated liquor 6 throughout the operation of the process.

The wet biomass obtained during the separation is then pretreated in a pretreatment zone 7, from which one or more liquid streams 8 are withdrawn.

According to a particular embodiment, the features of the liquid streams 8 are measured by means of sensors (pH, conductivity, flow rate, etc.) and the amounts of acid and/or of water introduced via pipes 3 and 4 are adjusted so as to keep constant the acidic power of said liquid streams 8 throughout the operation of the process.

Figure 3:
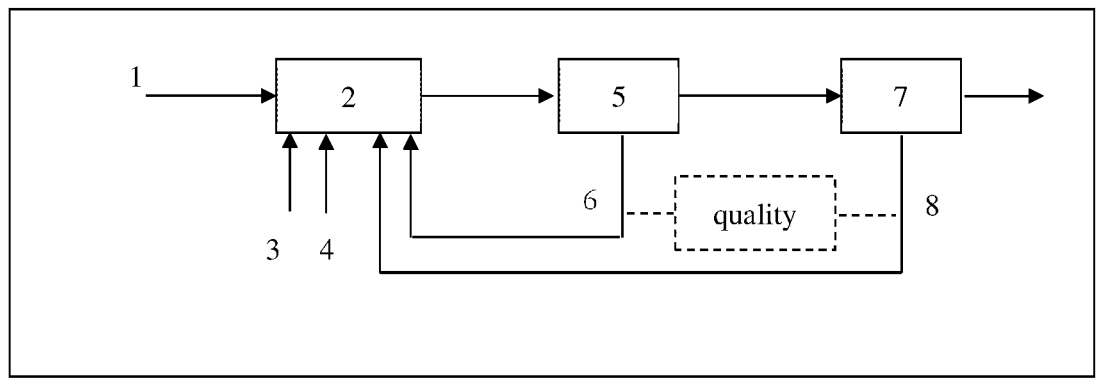
Figure 4:
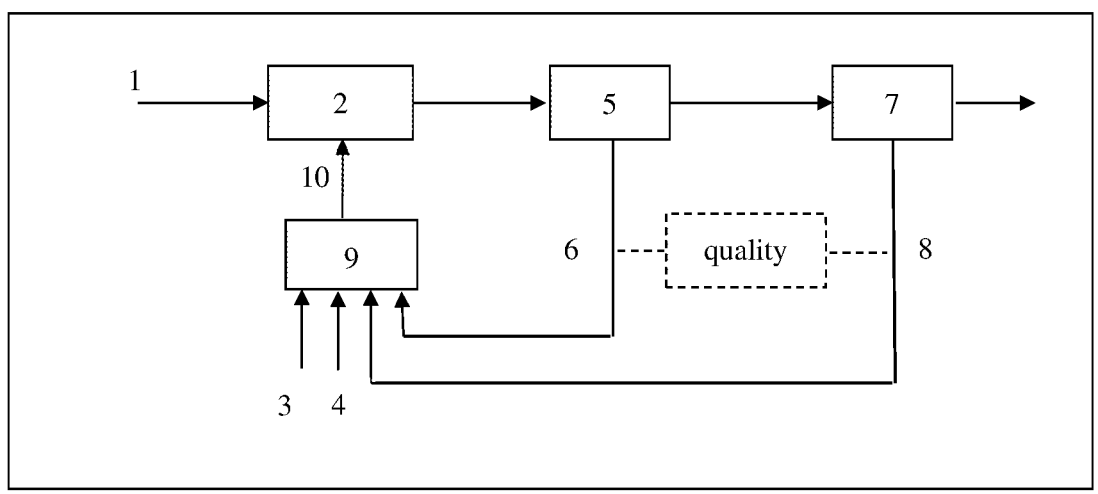

FIGS. 3 and 4 illustrate the possible recycling of the separated liquor 6 and/or of the liquid streams 8 into the impregnation zone 2.

EXAMPLES

Example 1

Example 1 presents the procedure according to the prior art. The biomass (wheat straw) is placed in contact with an acidic liquor (water+sulfuric acid) of controlled acidity (1.1 wt %). The biomass thus impregnated is pretreated by cooking in a steam explosion reactor (190° C., residence time of 5 minutes). By controlling only the acidity of the liquor introduced into the impregnation step, the variations in the quality of the biomass induced variations in the quality of the pretreated product. The following table illustrates this phenomenon. The two tests were performed on wheat straw under the same conditions: the results demonstrate the intrinsic variability of the feedstock.

|  | Straw Test 1 | Straw Test 2 |
|---|---|---|
| Acidity of acidic liquor | 1.1 wt % | 1.1 wt % |
| pH of press liquor | 1.6 | 1.8 |
| Conductivity of press liquor (mS/cm) | 12 | 20 |
| Content of monomeric and oligomeric sugars in the pretreated biomass | 50.3% | 64.8% |

For an acidity at 1.1 wt %, the production of monomeric and oligomeric sugars may range from 50 wt % to 65 wt % after the pretreatment step, due to the variability of the treated biomass. A substantial variation in the quality of the spent impregnation liquor (press liquor), of 0.2 pH unit and 8 mS/cm on the conductivity, is also observed. This variation in the quality of the spent liquor is directly responsible for the variability in the sugar content of the finished product.

Example 2

Example 2 presents the procedure according to the invention. The biomass (wheat straw) used in example 1 is placed in contact with an acidic liquor (water+sulfuric acid). The impregnated biomass is introduced into the pretreatment reactor by means of a screw, generating a liquid stream known as the press liquor. In the implementation according to the invention, the acid content of the impregnation liquor is adjusted so as to keep the quality of the press liquor (pH or conductivity) constant.

The table below illustrates the results of this procedure for a production of several days.

|  | Test 3 | variation |
|---|---|---|
| pH of press liquor | 0.61 | ±0.1 |
| Conductivity of press liquor (mS/cm) | 33.5 | ±3.2 |
| Content of monomeric and oligomeric sugars in the pretreated biomass | 68.7% | ±5% |

Regulating the press liquor (pH to ±0.1 or conductivity to ±10%) made it possible to limit the variability in the quality of the pretreated biomass to ±5 points of yield of sugars (monomeric and oligomeric). The use of the method of regulating the acidic liquor according to the invention thus makes it possible to ensure a constant quality of the finished product.

The invention claimed is:

1. A process for the continuous treatment of a lignocellulosic biomass for the production of sugary liquors, said process comprising:
   a) impregnating the biomass using an impregnation liquor with a pH of between 0.1 and 7, by placing said biomass in contact with said impregnation liquor,
   b) separating the impregnated biomass obtained in a) so as to produce a wet biomass with a solids content of at least 15% by weight, and a separated liquor,
   c) pretreating the wet biomass obtained in b) to produce a pretreated biomass, in the course of which one or more liquid streams are withdrawn,
   d) analyzing (i) the composition of the separated liquor obtained from b), (ii) the composition of one or more of the liquid streams withdrawn during c) the pretreating of the wet biomass, or (iii) the composition of the separated liquor obtained from b) and one or more of the liquid streams withdrawn during the pretreating of the wet biomass in c), and
   e) adjusting the composition of the impregnation liquor used in a) so as to keep constant the acidic power, corresponding to the amount of H$^+$ ions present, of (i) said separated liquor obtained from b), (ii) said one or more liquid streams withdrawn during the pretreating of the wet biomass in c), or (iii) both, throughout the process,
   wherein the impregnation liquor comprises at least one acid, and optionally water, and
   wherein adjusting of the composition of the impregnation liquor is performed by adding water, acid, or both to said impregnation liquor used in a), so as to keep constant, throughout the process, the acidic power of the separated liquor obtained from b) or the acidic power of the one or more liquid streams withdrawn during pretreating of the wet biomass in c), or both.

2. The process as claimed in claim 1, further comprising a step of preparing the impregnation liquor prior to a).

3. The process as claimed in claim 1, wherein a) is performed at a temperature ranging from 10 to 95° C., and the residence time of the biomass in said impregnation step is between 20 seconds and 12 hours.

4. The process as claimed in claim 1, wherein the impregnation liquor has a pH of between 0.1 and 6.

5. The process as claimed in claim 1, wherein the impregnation liquor is an aqueous solution of sulfuric acid, hydrochloric acid, or nitric acid, having an acid content of between 0.5% and 8% by weight of acid relative to the total weight of the liquor.

6. The process as claimed in claim 1, wherein b) is performed by draining, decantation, centrifugation, or pressing of the impregnated biomass.

7. The process as claimed in claim 1, wherein the solids content of the wet biomass obtained in step b) is between 25% and 70% by weight.

8. The process as claimed in claim 1, wherein pretreating the wet biomass in c) is performed by cooking.

9. The process as claimed in claim 1, wherein d) comprises measurement of the acidic power of said separated liquor obtained from b), one or more of said liquid streams withdrawn during pretreating of the wet biomass in c), or both, throughout the process.

10. The process as claimed in claim 9, wherein measurement of the acidic power is performed by measuring the pH or by measuring the conductivity, the measurements being performed either continuously or at a given frequency.

11. The process as claimed in claim 1, wherein said liquid streams withdrawn during pretreating of the wet biomass in c) are liquid streams withdrawn downstream of a) and upstream of subsequent biomass treatment steps.

12. The process as claimed in claim 1, further comprising recycling (i) the separated liquor obtained from b), (ii) the one or more liquid streams withdrawn during pretreating of the wet biomass in c), (iii) liquid streams withdrawn during subsequent biomass treatment steps, or (i), (ii), and (iii) into a).

13. The process as claimed in claim 1, further comprising, after the pretreating in c), treating at least a part of the pretreated biomass, by enzymatic hydrolysis, to produce said sugary liquors.

14. The process as claimed in claim 1, wherein at least one portion of the sugary liquors is subjected to an alcoholic fermentation.

15. The process as claimed in claim 1, wherein the impregnation liquor has a pH of between 0.1 and 2.

16. The process as claimed in claim 1, wherein the solids content of the wet biomass obtained in step b) is between 40% and 65% by weight.

17. The process as claimed in claim 1, wherein pretreating the wet biomass in c) is performed by steam explosion.

18. The process as claimed in claim 1, wherein adjusting of the composition of the impregnation liquor is performed by adding water or acid to said impregnation liquor used in a), so as to keep constant, throughout the process, the acidic power of the separated liquor obtained from b) or the acidic power of the one or more liquid streams withdrawn during pretreating of the wet biomass in c) to within ±10%.

19. The process as claimed in claim 1, further comprising recycling (i) the separated liquor obtained from b) into a).

* * * * *